(12) United States Patent
Adams

(10) Patent No.: US 8,083,666 B2
(45) Date of Patent: *Dec. 27, 2011

(54) ENDOSCOPIC RESECTION DEVICES AND RELATED METHODS OF USE

(75) Inventor: Ronald D. Adams, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 966 days.

This patent is subject to a terminal disclaimer.

(21) Appl. No.: 11/332,443

(22) Filed: Jan. 13, 2006

(65) Prior Publication Data

US 2006/0135849 A1  Jun. 22, 2006

Related U.S. Application Data

(60) Continuation of application No. 10/639,229, filed on Aug. 12, 2003, now Pat. No. 7,014,646, which is a division of application No. 09/939,407, filed on Aug. 24, 2001, now Pat. No. 6,632,227.

(51) Int. Cl.
*A61B 1/00* (2006.01)
(52) U.S. Cl. ........................ 600/104; 600/127
(58) Field of Classification Search .......... 600/104–106, 600/127, 175, 123, 116; 227/180.1; 606/1, 606/39, 41, 45, 46
See application file for complete search history.

(56) References Cited

U.S. PATENT DOCUMENTS

| | | | | |
|---|---|---|---|---|
| 5,085,659 A * | 2/1992 | Rydell | | 606/47 |
| 5,366,463 A * | 11/1994 | Ryan | | 606/159 |
| 5,669,918 A * | 9/1997 | Balazs et al. | | 606/139 |
| 5,938,586 A * | 8/1999 | Wilk et al. | | 600/123 |
| 6,119,913 A * | 9/2000 | Adams et al. | | 227/176.1 |
| 6,126,058 A * | 10/2000 | Adams et al. | | 227/180.1 |
| 6,142,931 A * | 11/2000 | Kaji | | 600/114 |
| 6,264,086 B1 * | 7/2001 | McGuckin, Jr. | | 227/180.1 |
| 6,302,311 B1 * | 10/2001 | Adams et al. | | 227/176.1 |
| 6,344,028 B1 * | 2/2002 | Barry | | 604/96.01 |
| 6,383,145 B1 * | 5/2002 | Worm et al. | | 600/564 |
| 6,398,795 B1 * | 6/2002 | McAlister et al. | | 606/139 |
| 6,468,203 B2 * | 10/2002 | Belson | | 600/146 |
| 6,468,227 B2 * | 10/2002 | Zimmon | | 600/564 |
| 6,491,719 B1 * | 12/2002 | Fogarty et al. | | 623/1.37 |
| 6,565,583 B1 * | 5/2003 | Deaton et al. | | 606/159 |
| 6,632,227 B2 * | 10/2003 | Adams | | 606/110 |
| 6,716,233 B1 * | 4/2004 | Whitman | | 606/219 |
| 6,805,129 B1 * | 10/2004 | Pless et al. | | 128/898 |
| 6,821,264 B1 * | 11/2004 | Khurana et al. | | 604/46 |
| 7,014,646 B2 * | 3/2006 | Adams | | 606/159 |
| 7,300,445 B2 * | 11/2007 | Adams | | 606/167 |

(Continued)

*Primary Examiner* — John P Leubecker
*Assistant Examiner* — Victoria Chen
(74) *Attorney, Agent, or Firm* — Fay Kaplun & Marcin, LLP

(57) ABSTRACT

Described is a tissue resection system which includes a guide element; a resection head; a positioning mechanism and an actuating mechanism. The resection head includes a guide channel slidably receiving the guide element and an endoscope channel sized to slidably receive an endoscope therein, so that, when the resection head is slid along the guide element, the endoscope and the resection head follow a path defined by the guide element. The positioning mechanism moves the resection head relative to a distal end of the endoscope between a first position in which the distal end of the endoscope extends distally out of the endoscope channel and a second position in which the distal end of the endoscope is received within the endoscope channel. The actuating mechanism moving a portion of an outer wall of the resection head to open and close a resection chamber defined by the outer wall.

15 Claims, 5 Drawing Sheets

U.S. PATENT DOCUMENTS 7,556,633 B2 * 7/2009 Lindsay .................. 606/159
7,882,995 B2 * 2/2011 McAlister et al. ......... 227/175.1
2004/0133228 A1 * 7/2004 Bayer .................... 606/190
2009/0149716 A1 * 6/2009 Diao et al. .............. 600/202

* cited by examiner

US 8,083,666 B2

ENDOSCOPIC RESECTION DEVICES AND RELATED METHODS OF USE

PRIORITY CLAIM

The present application is a Continuation application of a U.S. patent application Ser. No. 10/639,229 filed Aug. 12, 2003, now U.S. Pat. No. 7,014,646 entitled "Endoscopic Resection Devices and Related Methods of Use" which is a Divisional application of U.S. patent application Ser. No. 09/939,407, filed Aug. 24, 2001, now U.S. Pat. No. 6,632,227, entitled "Endoscopic Resection Devices and Related Methods of Use". The entire disclosures of these prior patents/applications, are considered as being part of the disclosure of the accompanying application and are hereby expressly incorporated by reference herein.

1. FIELD OF THE INVENTION

The present invention relates generally to full-thickness resection devices (FTRDs) and methods of using such devices to perform localized resections of lesions in organs, for example, substantially tubular organs such as the colon. The present invention has particular application to transanal and transoral surgical procedures, although it is not limited thereto.

2. DESCRIPTION OF THE RELATED ART

Resection procedures involve excising a portion of an organ, approximating the surrounding tissue together to close up a hole created thereby, and removing any excess tissue caused by the approximation. Various conventional devices and procedures are available for resecting lesions in substantially tubular organs.

For example, several known resection devices and procedures require at least one incision in an area near the portion of the organ to be excised. The incision is required to allow the physician to access the organ section to be excised and guide the device to that section. The incision permits access to the lesion or treatment site for these resection devices which do not have sufficient steering and/or viewing capabilities to appropriately access the site without such a surgical opening thereto. Thus, when an organ section to be excised is beyond the reach of such a device, or the device is not flexible enough to wind through the organ to the site to be excised, an incision will be required to position the device for the procedure. Of course, incisions are traumatic to the patient and may involve a partial or entire loss of mobility to the patient while recuperating from the incision, in addition to recovering from the resection procedure itself. The time required to recover from such a procedure also is often longer than for procedures which do not require incisions.

One type of conventional resection procedure utilizes a circular stapling instrument in which a tubular section of a tubular organ (in other words, a length of the organ) is excised, resulting in the tubular organ being separated into first and second segments. The end sections of the first and second segments are tied closed, in for example a purse-string fashion, and stapled together. The tissue of the "purse-stringed" end sections radially inside the line of staples is then cut off. In this circular anastomosis procedure, at least one separate invasive incision is typically made near the section to be excised in order to cut out the section to be removed and to pursestring the ends of the first and second sections of the organ. Also, a separate incision may be needed to place a first part of the resection device in the first segment and a corresponding second part of the device in the second segment (e.g., anvil in one segment and stapling head in the other) so that the device may bring the first and second segments together and staple them together. Thus, this type of resection procedure involves the drawbacks mentioned above in regard to procedures requiring invasive incisions as well as additional complications resulting from the removal of an entire tubular segment of the organ including, for example the risk of spillage of nonsterile bowel contents into the sterile body cavity, which can cause severe infection and possibly death.

An alternative resection device includes a stapling and cutting assembly on a shaft which can be bent or formed into a desired shape and then inserted into a patient's body cavity. Once the shaft has been bent into the desired shape, the rigidity of the shaft ensures that shape is maintained throughout the operation. This arrangement limits the effective operating range of the device as the bending of the shaft into the desired shape before insertion and the rigidity of the shaft once bent require the physician to ascertain the location of the organ section to be removed before insertion, and deform the shaft accordingly. Furthermore, the rigidity of the shaft makes it difficult to reach remote areas, particularly those areas which must be reached by a winding and/or circuitous route (e.g., the sigmoid colon). Thus, an incision may be required near the organ section to be excised in order to position the device at that organ section.

Furthermore, devices have been described in U.S. Pat. Nos. 6,119,913 and 6,126,058 including resectioning means guided through the colon using a flexible endoscope. Although these devices describe the removal of lesions beyond the splenic flexure of the colon, removals in these locations are limited to pendunculated-type polyps a stem of which may be severed by a snare or very small polyp-type tumors that can be removed using what are essentially biopsy devices (limited to mucosal depth only).

To help describe this, FIG. 1 shows the general shape of a portion of a colon 10 up to the cecum. The colon 10 has the following main sections: the rectum 11, the sigmoid colon 12, the descending colon 13, the splenic flexure 14, the transverse colon 15, the hepatic flexure 16, the ascending colon 17, and the cecum 18. The small bowel 19, or ilium, connects to the cecum 18, as shown in FIG. 1. Prior art resection devices purport to navigate the colon 10 up to the splenic flexure 14, but no further due to the right angle turn at the splenic flexure. Turns within the sigmoid colon 12 are described as being navigated and straightened by current endoscopy techniques allowing these devices to travel past the sigmoid colon 12. However, existing resection devices, which do not have steering capability or sufficient flexibility, must be pushed along the colon and rely on the colon wall to guide them. Pushing beyond the splenic flexure 14 significantly increases the risk of damaging the colon by, for example, tearing its wall. Thus, lesions beyond the splenic flexure that cannot be removed with a simple biopsy device are typically removed by open or laparoscopic surgery. To do so, a colonoscope is inserted in the rectum and guided to the section of the colon where the lesion is located. That section of the colon then is marked with a dye so the surgeon may determine what tissue is to be removed during surgery.

SUMMARY OF THE INVENTION

The present invention is directed to a resection head for endoscopic resection of tissue comprising an endoscopic receiving channel extending therethrough so that an endoscope may be slidably received therein and a first position adjusting mechanism for moving the resection head relative to an endoscope received in the endoscope receiving channel between a first retracted position in which a distal end of the endoscope extends beyond a distal end of the resection head and a deployed position in which the distal end of the endoscope is received within the endoscope receiving channel. The resection head also comprises a resection chamber within an outer wall of the resection head, at least a first portion of the outer wall being moveable with respect to a second portion thereof to open the resection chamber to an exterior of the resection head and a resection mechanism for resecting tissue received within the resection chamber.

The present invention is also directed to a method of resecting tissue comprising the steps of coupling a distal end of a flexible guide to a desired location on a wall of a body lumen and sliding a resection head coupled to an endoscope over the guide to the desired location, wherein the resection head is coupled to an endoscope with the flexible guide extending outside of the endoscope between an entrance to the body lumen and the desired location. A selected portion of tissue to be resected is then drawn into a resection area of the resection head and resected.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

The surgical resection devices according to the present invention will be shown and described with reference to use within the colon. The uses, however, are not so limited, as the devices may be used in various other hollow organs throughout the body, including, for example, the esophagus, stomach, and small bowel.

The present invention provides endoscopic surgical devices and related methods of their use that permit the devices to navigate a tortuous body lumen, including its sharp turns, through the use of a guide, such as a guidewire, for example. Instead of using the body lumen itself to guide the endoscope and resection device, the guidewire may be used to define a path allowing the resection device to navigate sharp turns without impinging upon the wall of the lumen to avoid damage to the organ wall.

Figure 1:
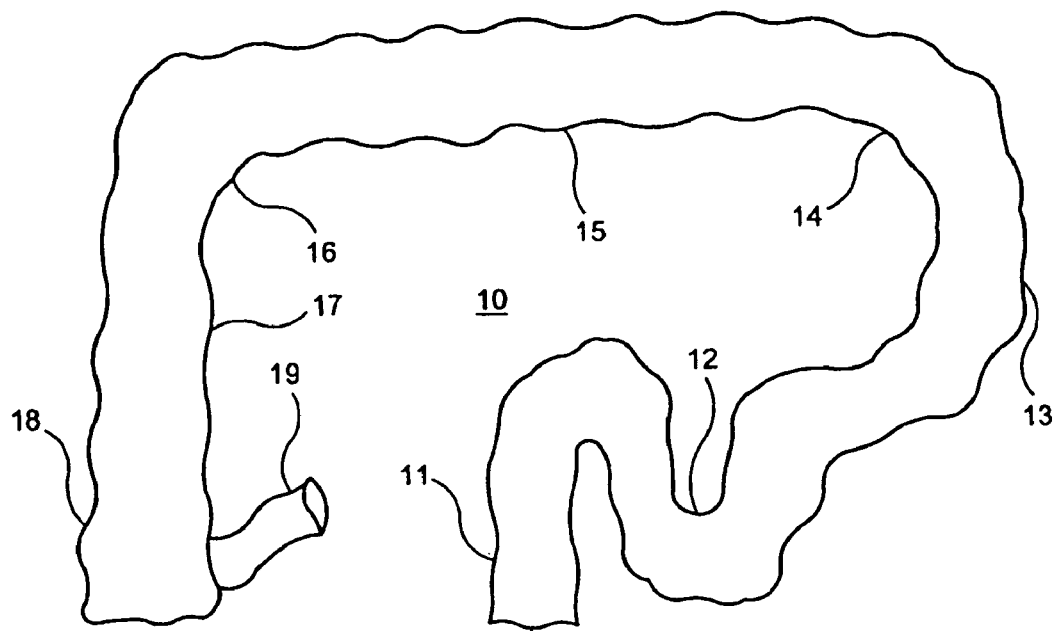
FIG. 1 is a plan view showing the various portions of a colon.
Figure 2:
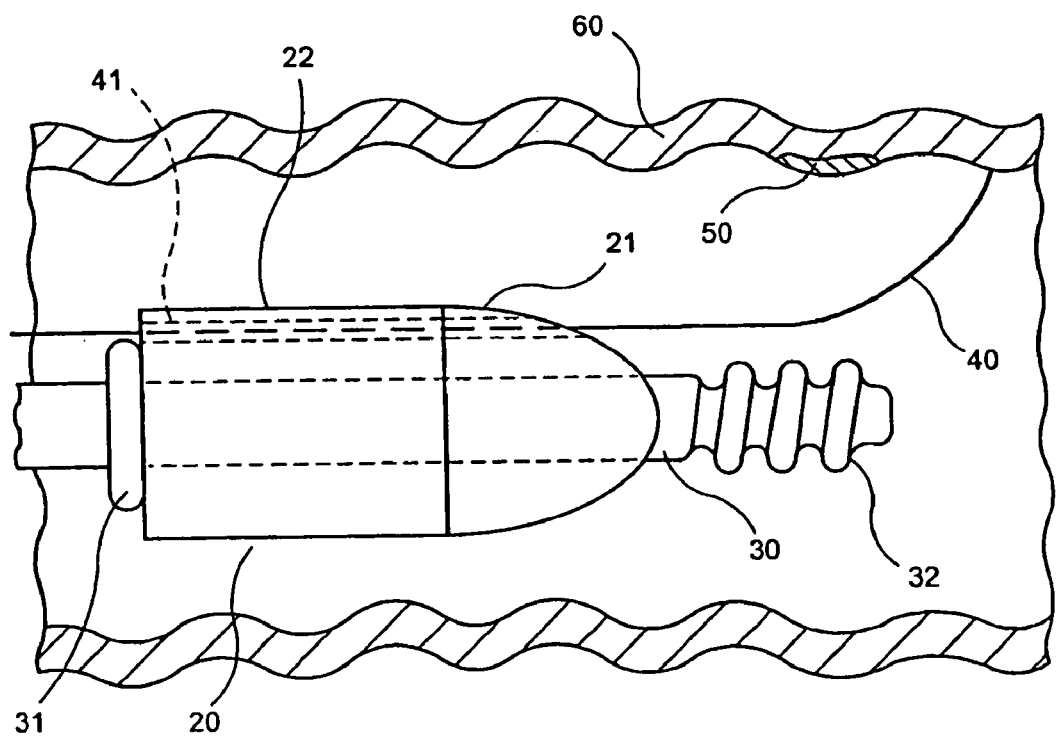
FIG. 2 is a cross-sectional view of the colon showing an FTRD according to an embodiment of the present invention along with a guidewire affixed to a portion of the colon near a lesion to be resected.

FIG. 2 shows an FTRD 20 according to an embodiment of the present invention. FTRD 20 is shown on a distal end of an endoscope 30. FTRD 20 has a rounded head 21 to allow for easier and safer navigation through the colon. A body portion 22 of FTRD 20 sits adjacent and proximal to head 21 and during navigation rests against a stop ring 31 located in a fixed position on endoscope 30. This stop ring may be made of a plastic or any other suitable biocompatible material known in the art.

A guidewire 40 is anchored to the colon wall 60 in a location near a lesion 50 (shown as a diseased portion of colon wall 60) to be resected. FTRD 20 is capable of resecting a range of lesion types, such as polyps or other types of lesions known to occur in body lumens. FTRD 20 of the current invention may be especially useful in resecting lesions, such as lesion 50, that previously could be removed only using invasive surgical techniques.

In practice, an operator may use a colonoscope (not shown) to navigate to the area of lesion 50, in a conventional fashion as is known in the art. Once the target area has been located using the colonoscope, a guidewire 40 may be inserted therethrough to this target area. Of course, the guidewire 40 may be inserted within the colonoscope as the colonoscope is maneuvered to the target area. However, this may make it more difficult for the operator to freely maneuver the colonoscope along the route to the target area. Preferably, the colonoscope is guided through the colon 10 to the location of lesion 50 and then guidewire 40 is inserted afterwards. Once the operator has located lesion 50 using techniques common with the use of a colonoscope, guidewire 40 may be affixed to the wall of the colon to act as a guide for FTRD 20 to reach the location of lesion 50. Guidewire 40 may be affixed to the colon wall using any suitable fixation device and method known in the art, including, for example, a hook, grasper jaw, suction, staple, or clamp adhesive. Once guidewire 40 has been anchored in place, the colonoscope may be removed.

Then an endoscope 30 with stop ring 31 mounted thereon and the FTRD 20 attached thereto distally of the stop ring 31 is inserted into the colon. A proximal end of the guidewire 40 is inserted into a guidewire channel 41 extending through the FTRD 20 and the operator may then insert the FTRD 20 and endoscope 30 into the colon with the guidewire 40 directing the path of travel as they are slid therealong. FTRD 20 and endoscope 30 may preferably be pushed along the length of the colon with the guidewire 40 defining the path along which they move therethrough. FTRD 20 may also be provided with any suitable, known advancing means to pull FTRD 20 and endoscope 30 along guidewire 40 to the desired location. However, while advancing the endoscope 30 and guidewire 40, tension on the guidewire 40 should be minimized to decrease the risk of inverting the colon.

Figure 3:
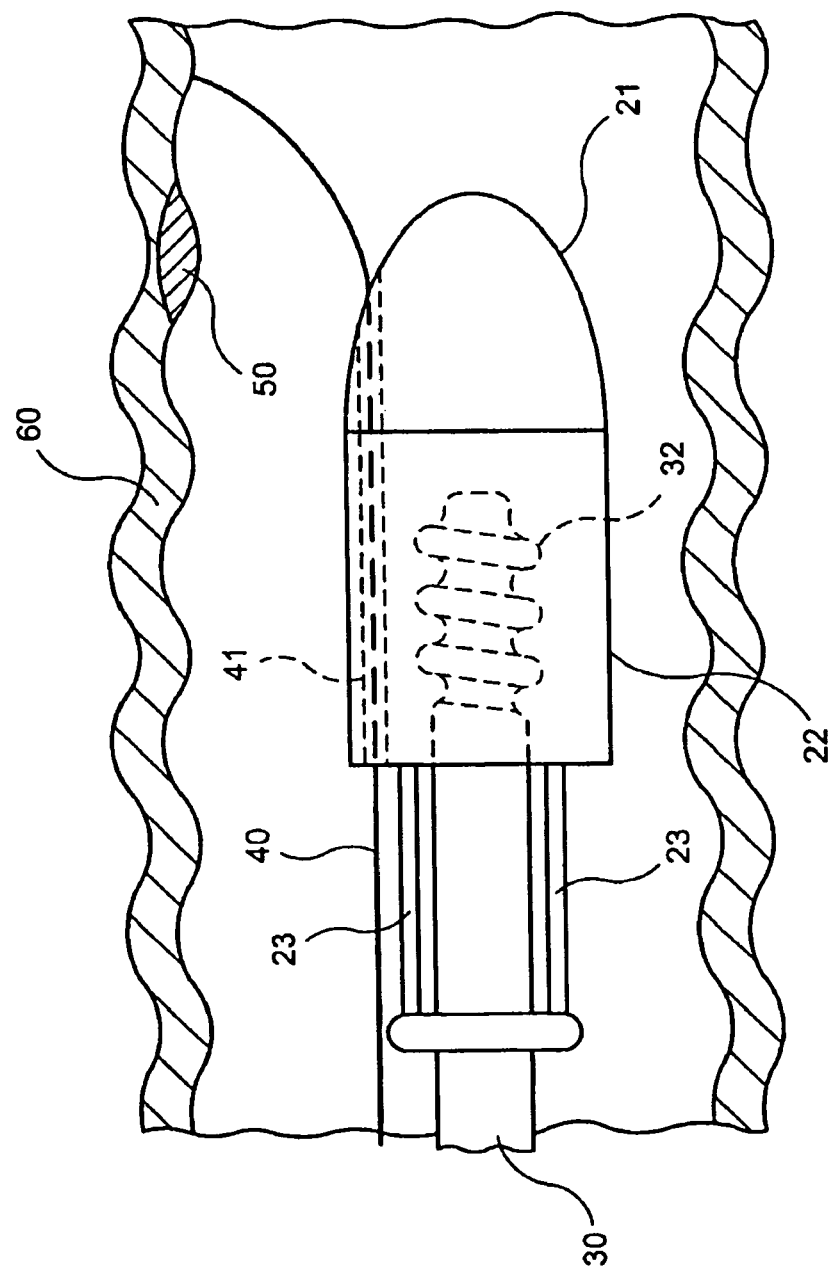
FIG. 3 is a cross-sectional view of the colon showing the deployed FTRD of FIG. 2.
Figure 4:
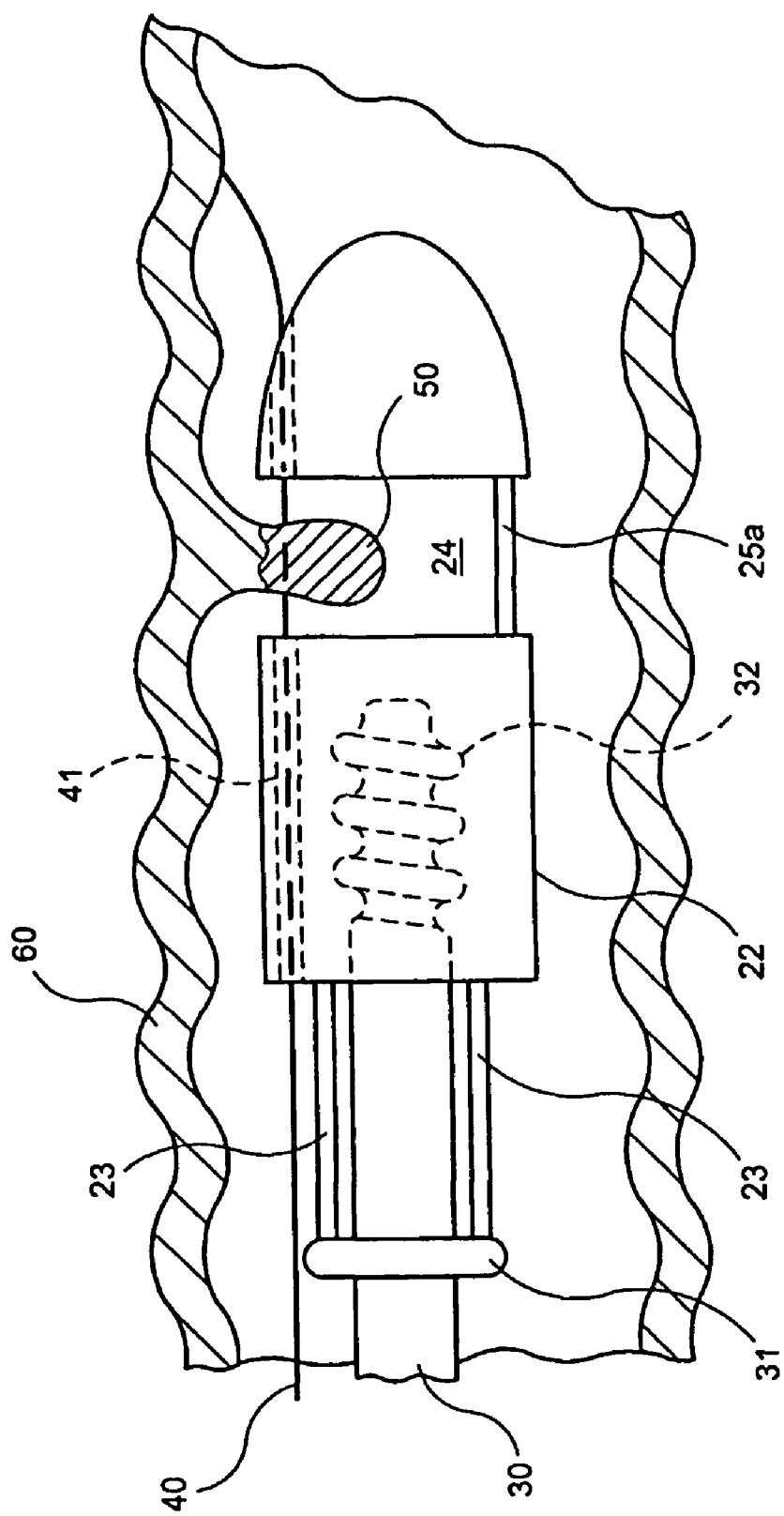
FIG. 4 is a cross-sectional view of the colon showing the deployed FTRD of FIG. 3 in a tissue receiving position.

As shown in FIG. 3, once FTRD 20 has reached lesion 50, it may be moved into a deployment position. Attached to stop ring 31 are two arms 23. These arms 23 allow FTRD 20 to extend past the distal end of endoscope 30 to a position proximate to lesion 50. Once in this position, a resection chamber may be opened to receive therein the tissue to be resected as will be described in more detail below. According to the present embodiment, arms 23 are activated by, for example, an hydraulic force applied via an actuator (not shown) located at a proximal end of the FTRD which remains accessible to the operator (i.e., outside of the patient) during the procedure. However, those of skill in the art will understand that the arms 23 may be extended to move FTRD 20 away from ring 31 by any of various actuating mechanisms such as, e.g., a cable and pulley mechanism, a rotating drive shaft and gearing mechanism, etc. In order to maintain a smooth outer profile of the body 23, prior to deployment, the arms 23 are received in channels (not shown) formed in the body 22. The operator then activates an arm 25a (which may also be actuated by, for example, hydraulic force) within FTRD 20 to separate head 21 from body 22 and open a resection chamber 24, as depicted in FIG. 4, to the interior of the organ. When the procedure has been completed, the operator may operate the arms 25a and 25b in the reverse direction using hydraulic force to close the resectioning chamber 24 and retract the FTRD 20 so that the distal end of the endoscope 30 protrudes therefrom.

Figure 5:
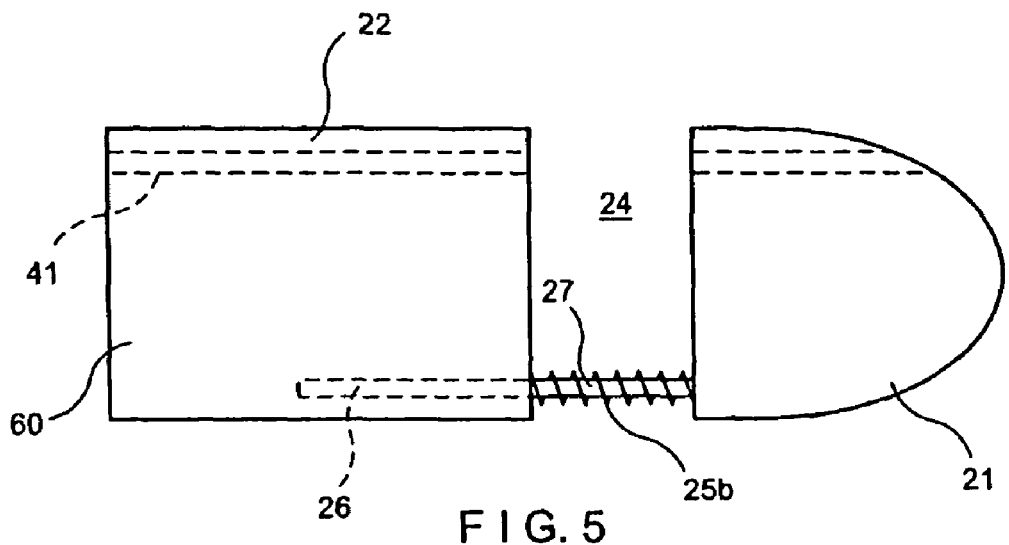
FIG. 5 is a plan view of another FTRD according to an embodiment of the present invention, with a spring loaded head extension arm.

As seen in FIG. 5, as an alternative to arm 25a, a shaft 25b may be fitted into an opening 26 within body 22 with a spring 27 received therearound biasing the head 21 into a separated configuration. A latch mechanism (not shown) maintains head 21 and body 22 together in a closed configuration until an operator releases the latch by, for example, actuating a pull cable (which extends to the proximal end of the device) allowing the spring 27 to expand and cause head 21 to separate thereby opening the resection chamber 24 to the interior of the organ.

Figure 4A:
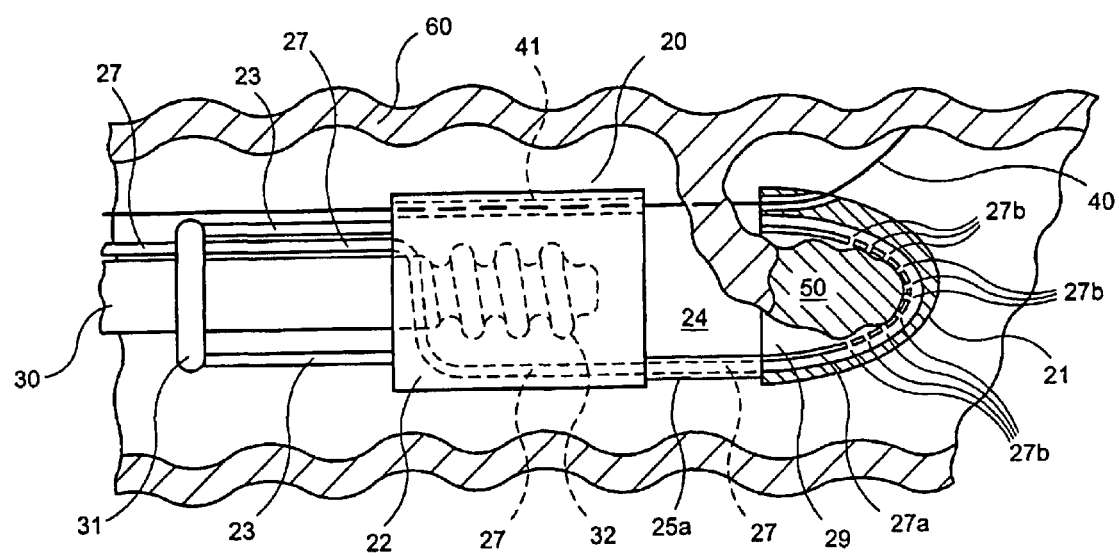
FIG. 4a is a cross-sectional view of the colon showing another embodiment of an FTRD according to the present invention, where a suction line is provided to apply suction to an internal cavity of a head of the FTRD for drawing a lesion into the head for resection.

Lesion 50 is then drawn into resection chamber 24 by any suitable means known in the art, such as applying suction to draw lesion 50 into resection chamber 24. This is depicted, for example, in an embodiment according to the present invention shown in FIG. 4a. In the FTRD 20 shown in FIG. 4a, head 21 may be provided with an open cavity 29 and a duct 27a containing one or more suction openings 27b. Duct 27a is connected to a vacuum source outside the patient via suction channel 27. Suction channel 27 may run through arm 25a (as shown in FIG. 4a) or it may run alongside arm 25a. Channel 27 then extends through body 22 and outside body 22 along or within endoscope 30. In this embodiment, an operator my activate the vacuum source thus creating suction at each of the suction openings 27b. This suction will then be used to draw lesion 50 into cavity 29 to then be resected.

Other means for drawing lesion 50 into resection chamber 24 may include a grasper used to grasp guidewire 40 and pull the lesion into chamber 24, or a snare used to grasp a knot or sinker affixed to guidewire 40 and retract lesion 50 into resection chamber 24 by pulling guidewire 40 into resection chamber 24.

Once lesion 50 has been drawn into the chamber 24, arm 25a may be actuated to close resection chamber 24 pinching the tissue surrounding the lesion 50 between the head 21 and the body 22. This tissue is then stapled together so that, when the lesion 50 is resected, the organ remains sealed. After the tissue has been successfully stapled, or otherwise joined together, the lesion and other tissue radially within the line along with the tissue is joined is resected and the FTRD 20 releases the stapled tissue so that the body 22 and the head 21 move to the fully closed position retaining the tissue of the lesion 50 therewithin so that it may be analyzed upon removal from the body.

The resection of the tissue may be performed by any suitable resection mechanism, such as, for example, providing a staple chamber within body 22 and an anvil within head 21 as is in current FTRD's. After resection of lesion 50, the operator may close the resectioning chamber 24 by retracting the arm 25a or 25b and then retract the FTRD 20 distally to the stop ring 31 by drawing the arms 23 back. The FTRD 20, endoscope 30, and guidewire 40 may then be removed from the patient with the resected tissue held in the resection chamber 24.

Head 21 may be made of a transparent material to allow the operator to make position adjustments even after the FTRD 20 has been configured in the deployed position with the distal end 32 of the endoscope 30 retracted therein. To make visual observations of the position of the FTRD 20, the end 32 of endoscope 30 may include light and visualization devices as are known in the art. The steerable and flexible distal tip of the endoscope 30 allows the operator to maneuver the tip look substantially distally through distal end of head 21 or to turn the tip away from a longitudinal axis of the endoscope 30 to view selected portions of the organ wall through the transparent head 21.

Figure 6:
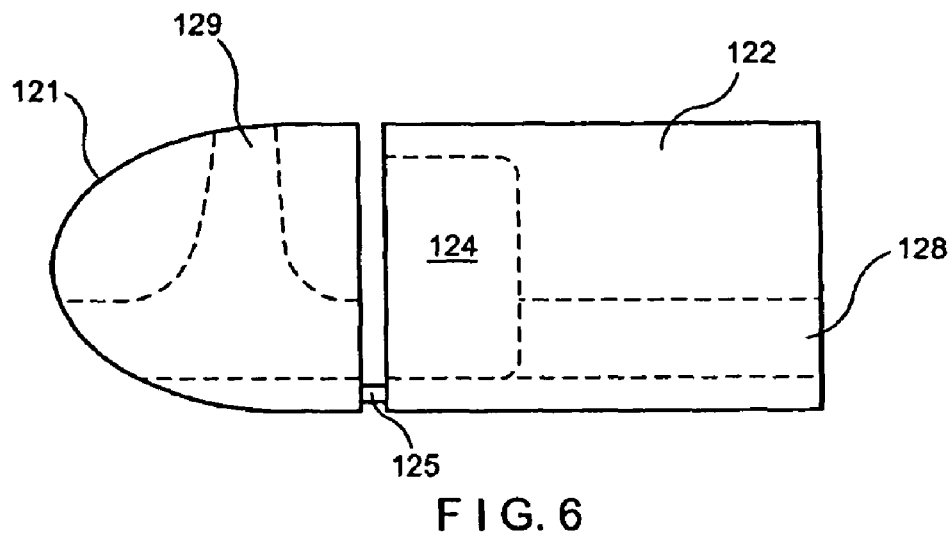
FIG. 6 is a plan view of another FTRD according to an embodiment of the present invention, with a radial viewing channel.

In another embodiment according to the present invention as seen in FIG. 6, a head 121 is formed of material which need not be transparent. However, an endoscope channel 128 is formed within head 121 and body 122, and a radial viewing port 129 is also formed in the head 121, as seen in FIG. 6. Port 129 may be either an open port or it may be covered by a transparent window. A resection chamber 124 may be opened by activating an arm 125.

Figure 7A:
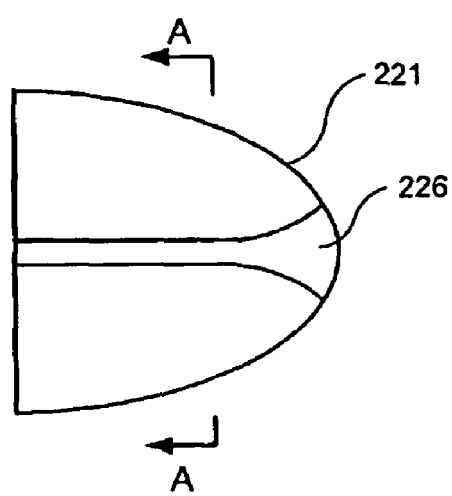
FIG. 7a is a plan view of yet another FTRD according to an embodiment of the present invention, with a guidewire channel formed into the head.
Figure 7B:
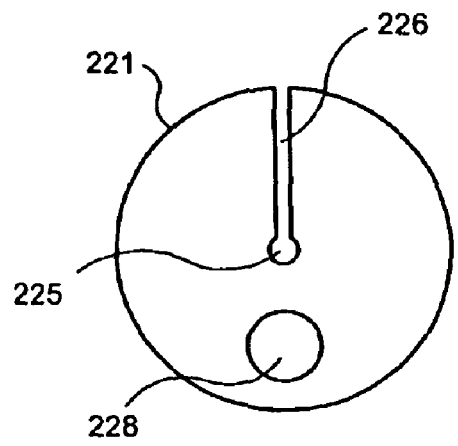
FIG. 7b is a cross-sectional view of the head shown in FIG. 7a taken through line A-A and rotated 90 degrees.

FIGS. 7a and 7b show a head 221 of an FTRD 20 according to another aspect of the invention. Head 221 includes an endoscope channel 228 and also a guidewire channel 225 that communicates with a groove 226 formed in head 221. While navigating the FTRD 20 through a body lumen, guidewire 40 may rest in channel 225. However, once the FTRD has reached the area of the lesion 50, the operator may wish to move the head 221 past the point at which the guidewire 40 is attached to the colon wall 60. By providing groove 226 in communication with channel 225, guidewire 40 may pass through groove 226 and out of head 221. This feature is especially advantageous when guidewire 40 is affixed to the colon wall at a location just beyond lesion 50 or proximal to lesion 50. If guidewire 40 is affixed at a location far enough past lesion 50, then guidewire channel 225 is sufficient and groove 226 is not needed, as guidewire 40 may still pass through the distal end of head 21 without interfering with the resection procedure and hindering the entrance of tissue into the resection chamber.

In another variation on the procedure for using any of the FTRD embodiments, guidewire 40 may be affixed directly to lesion 50. In this scenario, guidewire 40 may be used to pull lesion 50 into resection chamber 24. Once FTRD 20 is in position proximate lesion 50, the operator may pull guidewire 40 proximally into the FTRD 20 thereby drawing the lesion 50 into resection chamber 24. The procedure may then be completed as described above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A tissue resection system, comprising:
   a guide element;
   a resection head comprising a guide channel slidably receiving the guide element and an endoscope channel sized to slidably receive an endoscope therein, so that, when the resection head is slid along the guide element, the endoscope and the resection head follow a path defined by the guide element;
   a positioning mechanism moving the resection head relative to a distal end of the endoscope between a first position in which the distal end of the endoscope extends distally out of the endoscope channel and a second position in which the distal end of the endoscope is received within the endoscope channel, the positioning mechanism including arms advancing the resection head beyond the distal end of the endoscope; and
   an actuating mechanism moving a portion of an outer wall of the resection head to open and close a resection chamber defined by the outer wall.

2. The tissue resection system according to claim 1, further comprising a stop ring of the endoscope to limit translational movement of the resection head along the endoscope.

3. The tissue resection system according to claim 1, further comprising a resection mechanism disposed within the resection head.

4. The tissue resection system according to claim 1, further comprising a stapling mechanism for stapling together, prior to tissue resectioning, portions of tissue adjacent to tissue to be resectioned.

5. The tissue resection system according to claim 1, wherein the positioning mechanism comprises a hydraulic actuator.

6. The tissue resection system according to claim 1, wherein the positioning mechanism comprises at least one of a cable and pulley mechanism and a rotating drive.

7. The tissue resection system according to claim 1, further comprising a source of suction to draw tissue into the resection chamber.

8. The tissue resection system according to claim 1, further comprising a grasper to draw the tissue into the resection chamber.

9. The tissue resection system according to claim 1, further comprising a viewing port of the resection head providing an observation path from the endoscope.

10. The tissue resection system according to claim 9, wherein at least a portion of the outer wall is transparent.

11. A method of resecting tissue, comprising:
    advancing a resection head into a body lumen to a lesion along a guide element, the guide element engaging a guide channel of the resection head;
    monitoring progress of the resection head with an endoscope inserted through an endoscope channel formed in the resection head;
    moving the resection head distally relative to the endoscope via a positioning mechanism including arms to extend a distal end of the resection head beyond a distal end of the endoscope, adjacent to the lesion;
    moving a portion of an outer wall of the resection head to open a resection cavity formed therein;
    drawing tissue to be resected into the resection cavity; and
    resecting the tissue to be resected with a resection mechanism of the resection head.

12. The method according to claim 11, further comprising operating hydraulic actuators to move the resection head distally relative the endoscope.

13. The method according to claim 11, wherein the arms are operatively connected to the resection head.

14. The method according to claim 11, further comprising viewing the tissue to be resected via a viewing port of the resection head aligned with a field of vision of the endoscope.

15. The method according to claim 11, further comprising opening the resection cavity by releasing a spring biased to move the portion of the outer wall.

* * * * *